United States Patent
Raichle

(10) Patent No.: US 6,925,879 B2
(45) Date of Patent: Aug. 9, 2005

(54) VIBRATION ANALYZER AND METHOD

(75) Inventor: Kurt Raichle, Owatonna, MN (US)

(73) Assignee: SPX Corporation, Charlotte, NC (US)

(*) Notice: Subject to any disclaimer, the term of this patent is extended or adjusted under 35 U.S.C. 154(b) by 27 days.

(21) Appl. No.: 10/673,133

(22) Filed: Sep. 30, 2003

(65) Prior Publication Data

US 2005/0066730 A1 Mar. 31, 2005

(51) Int. Cl.[7] .............................................. G01N 29/12
(52) U.S. Cl. ........................... 73/579; 73/597; 73/659; 73/660
(58) Field of Search ..................... 73/579, 597, 599, 73/602, 659, 660, 593

(56) References Cited

U.S. PATENT DOCUMENTS

| | | | |
|---|---|---|---|
| 4,128,011 A * | 12/1978 | Savage | 73/579 |
| 4,429,578 A * | 2/1984 | Darrel et al. | 73/659 |
| 4,525,791 A * | 6/1985 | Hagiwara et al. | 700/280 |
| 4,843,885 A * | 7/1989 | Bambara | 73/660 |
| 5,144,838 A * | 9/1992 | Tsuboi | 73/579 |
| 5,511,422 A * | 4/1996 | Hernandez | 73/593 |
| 5,955,674 A * | 9/1999 | McGovern et al. | 73/650 |
| 6,234,021 B1 * | 5/2001 | Piety et al. | 73/592 |
| 6,456,945 B1 * | 9/2002 | Sonnichsen et al. | 702/56 |
| 6,507,790 B1 * | 1/2003 | Radomski | 702/39 |
| 6,681,634 B2 * | 1/2004 | Sabini et al. | 73/593 |
| 2003/0088346 A1 * | 5/2003 | Calkins et al. | |

* cited by examiner

Primary Examiner—Hezron Williams
Assistant Examiner—Jacques M Saint-Surin
(74) Attorney, Agent, or Firm—Baker & Hostetler LLP

(57) ABSTRACT

A tool and method to identify a defect in a vehicle through a vibration frequency is provided. To identify the defect in a vehicle, a sensor senses a vibration frequency and generates a signal in response to the vibration frequency. In addition, a signal spectrum analyzer communicates with the sensor and identifies the defect in response to the signal.

24 Claims, 2 Drawing Sheets

VIBRATION ANALYZER AND METHOD

FIELD

The present invention generally relates to a vibration analyzing device. More particularly, the present invention pertains to a vibration analyzer and method of diagnosing a mechanical problem utilizing sensed vibrations.

BACKGROUND

The repair of mechanical devices such as, for example automotive vehicles, includes the diagnosis of sounds and vibrations. The sources of these sounds and vibrations can be attributed to various components of the vehicle such as: the powertrain components, the engine, the transmission; the drive train, the drive shaft(s), flexible joints and bearings; the wheels and tires; air leaks in the passenger compartment; the exhaust system; the engine air induction system; plus many others.

These vibrations and noises must be diagnosed first as to source then as to cause. There currently does not exist a device that will lead the technician to either the source or cause of a vibration/noise. Existing diagnostics depend upon the technician being able to duplicate the conditions under which the vibration/noise was discovered, locate the portion of the vehicle that is the source of the vibration/noise, locate the component that is the source of the vibration/noise and correct the defect with the component that is causing the vibration/noise.

These vibrations/noises are dependent upon various factors associated with the vehicle itself such as vehicle speed, engine speed in revolutions per minute (RPM), application of the vehicle braking system, vehicle load condition, wheel and tire condition, and the like. Under these various conditions, each possible source of vibration/noise on the vehicle has a characteristic frequency or range of frequencies associated with it. These vehicle sources must be diagnosed separately from extra-vehicular sources such as the road surface, the weather (i.e., precipitation and wind), and the ambient noise levels around the vehicle.

Previous solutions for diagnosing vibration/noise involve amplifying the vibration/noise in an attempt to better discern the vibration/noise source or cause. These devices range from stethoscopes, both with and without a contact/probe component, to electronic amplification equipment. These solutions provide for better localization and amplification of the resulting sound/noise from a vibration to aid the technician in determining the location and probable cause of the vibration/noise symptom.

Diagnosis of vibrations and resulting sounds/noises is currently done by descriptive text provided by each original equipment/vehicle manufacturer (OEM). This text provides descriptions of vibrations and resulting sound/noise in loose terms such as "groan", "whistle", "squeal", and "thump." While these terms may indeed describe the vibration/noise precisely in the source language, they may be alien to the technician. It is understood that the translation of a term from the source language to the language of the technician may not also translate the distinction inherit in the original description of the term in the source language.

The terms used by the OEM to describe a vibration/noise may require the technician to identify a noise in terms that may be culturally alien to him/her. These terms may require the technician to think of the sounds/noises in terms that may not exist in the technician's lexicon or to think of the sounds/noises in a manner that may not apply to the technician's set of experiences.

The existing tools available to aid the technician in the diagnosis of vibration/noise do not discriminate between the various noises/sounds available on/in the vehicle. These available tools also do not assist the technician in determining the accurate description of the vibration/noise/sound being detected. The technician cannot accurately, efficiently and repeatedly diagnose the symptoms; determine the fault and repair/replace the correct component.

The existing tools, because of their generic nature, do not lend themselves to the accurate detection, diagnosis and repair of a source of vibration or noise. They work in the context in which they were developed, but are not universally applicable to produce the same results in the same application by all technicians. Their use is neither intuitive nor specific enough to be used in the same manner for the same purpose on the same symptom by all technicians.

Accordingly, it is desirable to provide a method and apparatus capable of overcoming the disadvantages described herein at least to some extent.

SUMMARY

The foregoing needs are met, to a great extent, by the present invention, wherein an apparatus and method is provided that is able to diagnose a mechanical problem in response to sensed vibrations.

An embodiment of the present invention pertains to a system for analyzing a vibration frequency in a vehicle having a defect. This system includes a sensor and a signal spectrum analyzer. The sensor senses the vibration frequency and generates a signal in response to the vibration frequency. The signal spectrum analyzer communicates with the sensor and identifies the defect in response to the signal.

Another embodiment of the present invention pertains to an adapter for analyzing vibration in a device having a defect. This adapter includes a receiver and a microprocessor. The receiver receives a signal generated in response to the vibration. The microprocessor uses a linear transform to identify a plurality of frequency components in response to the signal. In addition, the microprocessor determines a frequency component related to the defect and determines the defect.

Yet another embodiment of the present invention relates to an apparatus for analyzing a vibration of a device. This apparatus includes a means for sensing the vibration having a plurality of frequency components and a means for generating a signal corresponding to the sensed vibration. In addition, the apparatus includes a means for determining a frequency component having a relative maximum amplitude from the plurality of frequency components and a means for determining a probable faulty component of the device in response to the frequency component.

Yet another embodiment of the present invention relates to a method of analyzing a vibration of a device. In this method, the vibration, having a plurality of frequency components, is sensed and a signal corresponding to the sensed vibration is generated. In addition, a frequency component having a relative maximum amplitude is determined from the plurality of frequency components and a probable faulty component of the device is determined in response to the frequency component.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Various embodiments of the invention provide an accurate and relatively quick diagnoses of the source of a reported "noise" or "vibration". Known diagnostics rely upon conventions of speech and practice derived from personal experience and working on known vehicles. Given the extreme diversity in the vehicle market place as well as the diversity in the experience and background of the technicians servicing the vehicles, there exists a need to reliably and consistently diagnose those esoteric symptoms referred to as "noise" and "vibrations" by the vehicle or mechanical device operator.

Figure 1:
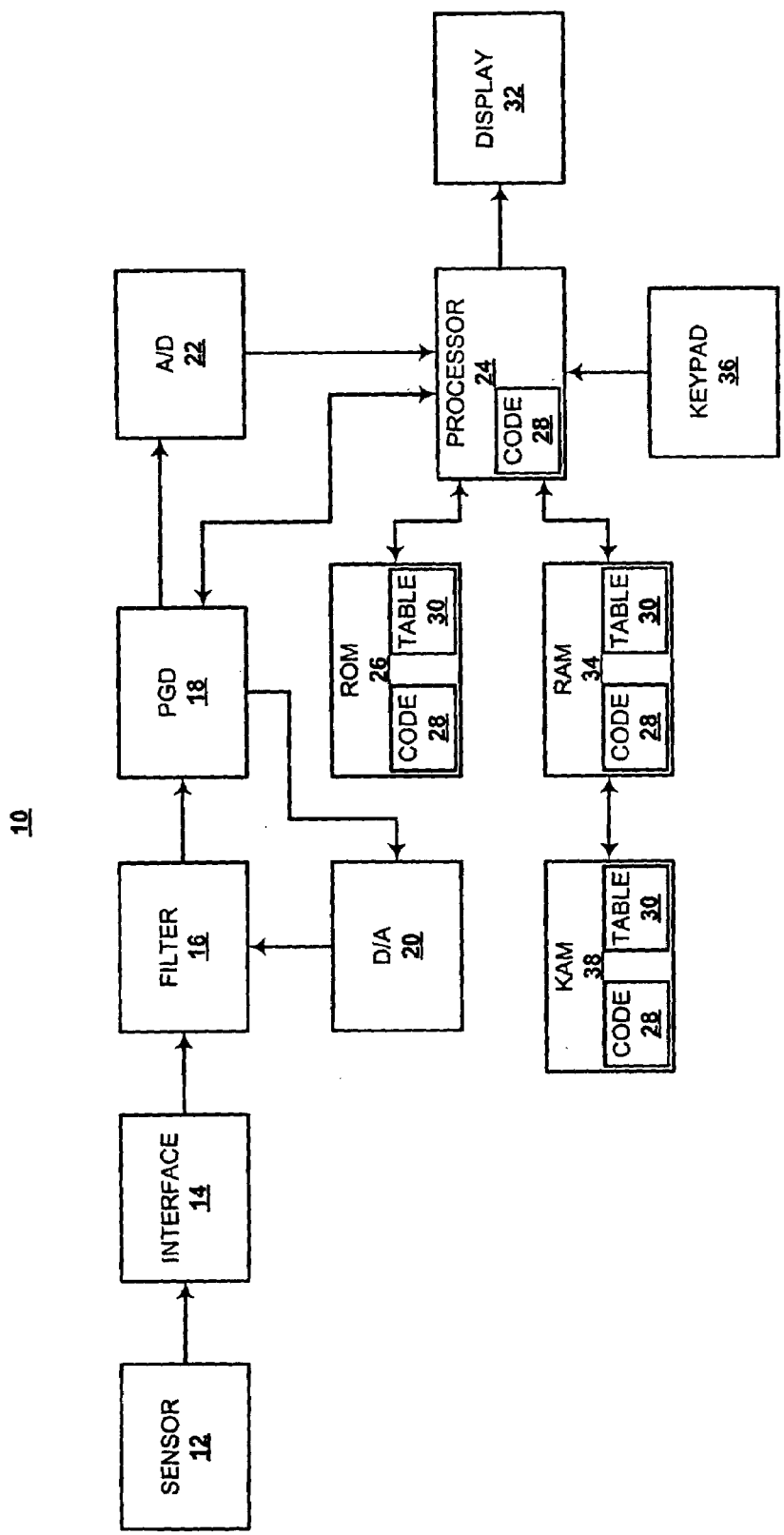
FIG. 1 is an illustration of a system for analyzing vibration according to an embodiment of the invention.

An embodiment of the invention will now be described with reference to the drawing figures, in which like reference numerals refer to like parts throughout. As shown in the preferred embodiment of FIG. 1, a vibration analyzer 10 includes a sensor 12, an interface 14, a frequency filter 16, a programmable gate device 18, a digital to analog (D/A) converter 20, an analog to digital (A/D) converter 22, a microprocessor 24, a read-only memory (ROM) 26, a recognition program 28, a look-up table 30, a display 32, a random access memory (RAM) 34, a keypad 36, and a keep-alive-memory (KAM) 38. The sensor 12 generates an electrical signal in response to a vibration, which may also be generating a noise/sound. The vibration caused noise may be within the hearing range of a human or either above or below the hearing range of a human. The vibration may have such an extremely low or high frequency that it may only be detected by touch rather than by sound, that is "felt" rather than "heard."

In various embodiments of the invention, the sensor 12 includes an accelerometer, a piezo-electric sensor, an omni-directional microphone, a directional microphone, and/or the like. In addition, it is within the scope of the invention that the various types of sensors are interchangeable within a single embodiment of the invention. In this manner, vibration from a multitude of varied sources may be analyzed. For example, the accelerometer are typically configured to detect relatively low frequency vibrations typically associated with changes in direction of one or more components. Whereas the piezo-electric sensor are generally configured to detect extremely high frequency vibrations. Such vibrations may be perceived as a "tingling" sensation while operating the vehicle rather than as a "noise" or a "sound." In contrast, the omni-directional microphone are typically capable of oscillating at the sound detection range of normal human hearing. In a manner similar to the omni-directional microphone, the directional microphone is typically sensitive to sounds around the sound detection range of human hearing, however, the directional microphone is utilized to isolate the location of the vibration/noise/sound source.

In the preferred embodiment, the sensor 12, selected to analyze the symptom, is variable to allow the diagnosis of vibrations over the widest possible spectrum. The sensor 12 is preferably attached to a driver/interface 14 capable of providing power to active sensors such as accelerometers. The interface 14 may also include the capability to provide a current to signal modifier devices such as microphones, as well as, accept signals from passive sensing devices such as piezo sensors generating their own power/signal from the action of vibration upon their structure. Generally, driver/interface devices 14 do not modify the signal from the sensing device, but rather, provide power or current to the sensing device. In this regard, the interface device 14 is configured to provide power to those sensors working in an active mode and requiring a power source, such as an accelerometer. In addition, the interface device is configured to provide isolation of the sensor 12 from the rest of the vibration analyzer 10 electronics.

The frequency filter 16 filters the frequency or range of frequencies to scan in response to controlling signals from the programmable gate device 18. This programmable gate device 18 or field programmable gate array typically controls the frequency filter 16 to pass a default range of frequencies and then generally modulates the frequency filter 16 to pass other ranges of frequencies. In an embodiment of the invention, the programmable gate device 18 is an essentially separate component in communication with the various other components of the vibration analyzer 10. However, in another embodiment, the capabilities of the programmable gate device 18, the A/D converter 22, and/or the D/A converter 20 are subsumed within the microprocessor 24.

Typically, frequency filters are controlled via analog signals. As these controlling signals are generally output from the programmable gate device 18 as digital signals, they are therefore converted to analog signals via the digital to analog (D/A) converter 20 prior to there arrival at the frequency filter 16.

The analog-to-digital (A/D) converter 22 is configured to convert the analog signal generated by the sensor 12 and passed through by the frequency filter 16 to a digital signal. The microprocessor 24 processes this digital signal in order to provide the information sought by the technician. For example, the microprocessor 24 is configured to execute the recognition program 28. By executing the instructions include within this recognition program 28, the microprocessor 24 is configured to receive the digitized signal from the A/D converter 22 and perform a linear transform such as Fast Fourier Transform (FFT) to segregate the primary signal frequency, that single frequency having the greatest amplitude, from the signals comprising the harmonics of this primary signal. In this manner, a discrete signal attributable to a single source is determined. The microprocessor 24 is further configured to utilize the primary signal frequency to query the look-up table 30. Based upon entries to the look-up table 30, the microprocessor 24 is configured to determine the source or probable faulty component responsible for generating the primary signal frequency. In response to this determination, the microprocessor 24 is configured to control the display 32 to display at least one of the primary signal frequency, the amplitude of the primary signal frequency, and/or the probable faulty component.

In an embodiment of the invention, the A/D converter 22, the microprocessor 24, and/or the display 32 are included in any suitable digital multimeter device or digital automotive tester. Examples of such suitable devices are produced by SPX/OTC Service Solutions of Owatonna Minn., U.S.A. In this regard, the various other components of the vibration analyzer 10 essentially form an adapter suitable for use with the digital automotive tester.

The vibration analyzer 10 may include sufficient read only memory (ROM) 26 to contain the recognition program 28 and at least one look-up table 30. The look-up table 30 may correlate the noises/vibrations to the root cause and source components. The intent of the recognition program 28 and its interrelationship to the look-up table 30 is to facilitate identifying vibration sources that generate vibrations that match the primary frequency detected by the invention. These sources are displayed to the technician by the display 32.

With regard to the one or more look-up tables 30 or sets of look-up tables 30, these may be developed from the existing diagnostics as provided by the original equipment manufacturers (OEM), developed empirically, and/or developed utilizing machine learning algorithms, data mining or knowledge acquisition software, and the like. In a particular example, the list of vibration sources are derived from a frequency/source match table generated from the existing diagnostics derived from the OEM diagnostic tables. Another source of these match tables includes the selections available to the technician using the vibration analyzer 10 to identify the vibration/noise producing component and choosing the appropriate frequency and amplitude as recorded by the vibration analyzer 10. These items may be correlated and directly stored to the look-up table 30 and/or processed by a data mining algorithm. Suitable examples of data mining software may include C5.0 available from RuleQuest Research Pty Ltd of St Ives Australia.

The current frequency amplitude may be stored in Random Access Memory (RAM) 34 in the vibration analyzer 10 as a case unit. The term, "case unit" generally refers to a job or work order. That is, when a vehicle is presented to the technician for repair, the vehicle is assigned a case unit that is associated with the vehicle throughout the repair process. Using the keypad 36, for example, the technician edits information associated with the case unit. This information includes, for example: the root source of the vibration; tests performed; parts replaced; time and date; and the like.

In an embodiment, the case unit is stored into the keep-alive-memory (KAM) 38, provided in the form of flash memory, in response to the vibration analyzer 10 receiving a shut down command.

Figure 2:
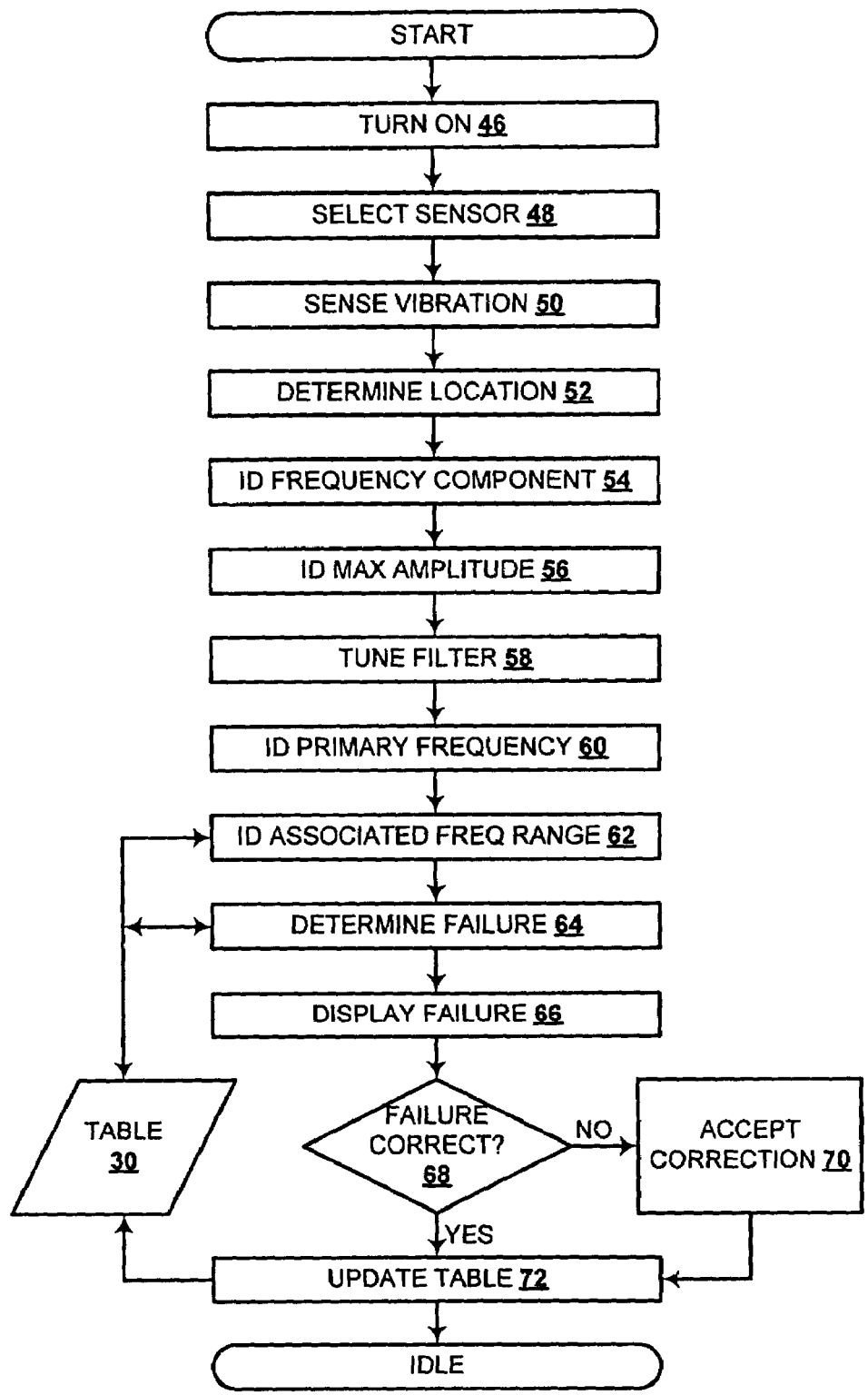
FIG. 2 is a flow diagram of a method according to an embodiment of the invention.

FIG. 2 is a flow diagram of a method 44 according to an embodiment of the invention. As shown in FIG. 2, the method 44, in this embodiment, is initiated by turning on the vibration analyzer 10 at step 46. For example, power is supplied to the various components of the vibration analyzer 10. In addition or alternatively, the method 44 may be initiated in response to a start command. For example, the user presses a start key on the keypad 36. In response to initiation, the microprocessor 24 begins receiving signal from the sensor 12. The use of the microprocessor 24 generally reduces variable and subjective assessments and thereby facilitates accurate and repeatable diagnosis of vibrations and noises. As described herein, in various embodiments of the invention, the sensor 12 includes one or more suitable vibration-sensing devices. Examples of suitable vibration sensing devices include directional microphones, omni-directional microphones, piezo-electric sensors, accelerometers, and the like. Furthermore, it is within the scope of the invention that these vibration sensing devices are interchangeable. In this manner, a variety of vibration types and locations may be accurately diagnosed.

At step 48, a suitable sensor 12 is selected by the technician. This selection process is generally determined in response to the type and/or location of the vibration. For example, in order to diagnose a noise heard in an interior compartment of the vehicle, a logical starting point may be to utilize an omni-directional microphone as the sensor 12. After establishing the frequency and amplitude of the noise heard, the technician typically changes to a directional microphone in order to localize the portion of the vehicle that contains the source of the noise.

For a reported vibration that produces a "tingling feeling" in the vehicle owner's hands, the technician generally initiates diagnosis with a piezo-electric sensor attached to the steering wheel. In this case, the vibrations might be too high to be audible, however, these vibrations may be recognized or identified via touch. If this is the case, then, the appropriate sensor 12 includes one capable of sensing the relatively high range frequencies afforded by the piezo-electric devices. The source for these high frequency vibrations may be a minute fracture in a bearing surface in the steering gear, for example.

For a reported "regular bouncing or floating sensation" the technician generally initiates diagnosis with an accelerometer as the sensor 12. These devices are capable of detecting the changes in direction indicated by the reported symptom. The source for this type on symptom may be a defective ride control system or an oscillation in an automated suspension system. These types of defects typically do not produce a "noise" but instead produce a very long period oscillation or vibration.

In addition, the sensor 12 may include a plurality of sensing devices as described herein. However, it is to be noted that it is within the scope of the invention that a single generalized sensor operable to detect a broad range of frequencies may be utilized as the sensor 12. Following selection of the sensor 12, vibration are sensed at step 50.

At steps 50 and 52, a location to sense the vibration is determined and the vibration is sensed. The particular order these steps are performed depends upon the particular circumstances. For example, if the general location of the source of the vibration is apparent, the technician determines the location to sense the vibration. Alternatively, if the source of the vibration is not apparent, the vibration is sensed at a plurality of locations to determine a suitable location. For example, the sensor 12, placed in or around the machine or vehicle being examined, senses any suitable vibration within the frequency response range of the sensor 12. The sensor 12 is then be moved to another location and the relative amplitudes of the sensed vibrations are compared. The location having the relatively louder sensed vibrations is determined to be the suitable location. In another example, a plurality of sensors are placed in or around the apparatus being examined. In this manner, the location of the source of the vibration is more readily determined. For example, a sensor 12 of the plurality of sensors 12 sensing the relatively loudest vibration is determined to be relatively closer to the vibration source. In another example, the location of the vibration source is determined based on a lag time of the vibration received at the various locations utilizing a triangulation algorithm.

At step 54, one or more frequency components are identified. In this regard, signals generated by the sensor 12, in response to any suitable vibrations, are transmitted from the sensor 12, through the various components of the vibration analyzer 10, and to the microprocessor 24. For example, an embodiment of the invention includes the interface device 14 or driver device 14 configured to receive signals from the sensor 12 and forward these signals to the microprocessor 24 via the filter 16, the programmable gate 18, and the A/D converter 22. Signals passing through the filter 16 are generally filtered. That is, the filter 16 is configured to pass a relatively discrete range of frequencies, such as high, medium, or low range frequencies. Initially, the filter 16 is generally configured to pass a default range, for example.

The signal from the sensor 12, after passing through the interface device 14 and the programmable filter/gate configuration 16/18, is processed by the analog-to-digital (A/D) converter 22. At this point, the signal is transformed into a digital format that can be accepted and acted upon by the microprocessor 24. For example, the A/D converter 22 is configured to convert the analog signal into at least two 16 bit bytes. This degree of specificity provides the microprocessor 24 the resolution to cover any reasonably suitable vibration capable of being heard or felt by a vehicle owner.

The microprocessor 24 is further configured to identify the plurality of frequency components in response to the signal. For example, the microprocessor 24 is configured to perform a linear transform such as Fourier transform, Laplace transform, and the like. In a more particular example, the microprocessor 24 utilizes a discrete Fourier transform, or a FFT. These or other transforms are utilized to decompose or separate a waveform or function into sinusoids of different frequency which sum to the original waveform. In this manner, the Fourier transform is utilized to aide in identifying and/or distinguishing the different frequency sinusoids and their respective amplitudes.

At step 56, the frequency component having the highest relative amplitude is determined. For example, in response to the frequency components identified at step 54, the microprocessor 24 compares these frequency components and determines the frequency component having the relative maximum amplitude. This maximum amplitude and/or its associated frequency component are communicated to the programmable gate 18, which in turn tunes the filter 16 via the D/A converter 20 at step 58.

At step 58, the filter 16 is tuned. As described herein, the filter 16 is configured to pass a relatively discrete range of frequencies, such as high, medium, or low range frequencies. While the filter 16 may initially pass a default range of frequencies, at step 58, the filter 16 is modulated, in response to controlling signals generated by the programmable gate 18, to allow other frequency ranges to pass through. The programmable gate 18 may be configured to control the filter 16 via a digital-to-analog (D/A) converter 20. The programmable gate 18 is configured to respond to the digital commands of the microprocessor 24. In particular, the maximum amplitude and/or its associated frequency component determined at step 56 are forwarded to the programmable gate 18 and utilized by the programmable gate 18 to modulate the filter 16.

At step 60, the microprocessor 24 determines the primary frequency within the band by performing another linear transform. In this manner, the microprocessor 24 distinguishes between the original vibration and the harmonic vibration set into play from the components attached to the original component having failed.

In various embodiments of the invention, these transformation are performed as a single step or a plurality of essentially discrete steps. When performed in a plurality of steps, the first step includes sampling the ambient vibration/noise in an interior compartment of the vehicle, for example, and establish the reference for this level against the sound decibel (db) level of conversation normally held in the interior compartment. Any signal having amplitude greater than the level of conversation is displayed to the technician as the logical starting point for diagnosis.

Given that any peak amplitude is composed of the sum of the amplitudes of the vibrations available, at step 62, the microprocessor 24 selects a range of frequencies surrounding the peak amplitude as a starting point in the diagnostic scenario. This range of frequencies is selected from the look-up table 30 stored in the read only memory (ROM) 26 for example.

At step 64, one or more probable causes of the vibration are determined. For example, the microprocessor 24 compares the sensed vibrations to a proscribed base level for the vehicle or apparatus. When the amplitude of the vibration/noise exceeds this level, the microprocessor 24 flags the frequencies exceeding the base level. These flagged frequencies are utilized to query the table 30 for associated defects or failures. These associated failures are displayed to the technician via the display 32 at step 66.

At step 68 it is determined whether the probable failure determine at step 64 is correct. For example, the technician may examine the suggested component or may determine that the particular vibration detected was caused by a different component. If, at step 68, it is determined that the probable failure is incorrect, the technician may enter the empirically determined faulty component into the vibration analyzer 10 via the input keypad 36, at step 70. For example, a unit case is generated for the vibrations detected. The technician may edit the unit case with the keypad 36 and review any findings on the display 32. These finding include empirically determined component failures and the like. In addition, the unit case along with these findings and vibrations detected are stored to memory such as the RAM 34 and/or KAM 38. This information is utilized to modify existing look-up tables 30 and/or generate a new look-up table 30. Thus, new sets of correlations between vibrations sensed and failed components are committed to memory or learned. In this manner, information entered by the technician is utilized to further develop the look-up table 30 and thus, increase the likelihood that probable faulty components determined by future iterations of the method 44 are correct. If, at step 68, it is determined that the probable faulty component determined at step 64 is the defective component then, at step 72, the look-up table 30 is updated accordingly. In this manner, correct determinations are reinforced, thereby improving the overall performance of the vibration analyzer 10. Following the step 72, the vibration analyzer 10 may idle until instructed to perform another analysis.

There has been outlined, rather broadly, the more important features of the invention. The descriptions and drawing are only illustrative of preferred embodiments that achieve the objects, features, and advantages of the present invention. It is not intended that the present invention be limited to them. Any modification of the present invention that comes within the spirit and scope of the descriptions and claims is considered to be part of the present invention.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for analyzing a vibration frequency in a vehicle having a defect, the system comprising:
   a sensor to sense the vibration frequency, wherein the sensor generates a signal in response to the vibration frequency;
   a signal spectrum analyzer in communication with the sensor, wherein the signal spectrum analyzer identifies the defect in response to the signal; and
   a table configured to provide the range of frequencies in response to a query, the query including the frequency component having the relative maximum amplitude.

2. The system according to claim 1, further comprising:
   a frequency selector in communication with the sensor and configured to select a frequency component having a relative maximum amplitude from a plurality of frequency components of the vibration frequency.

3. The system according to claim 2, wherein the frequency selector further comprises:
   a signal filter for filtering the signal.

4. The system according to claim 3, wherein the frequency selector further comprises:
   a programmable gate device for controlling the filter.

5. The system according to claim 2, wherein the signal spectrum analyzer comprises:
   a microprocessor that utilizes a linear transformer to identify the plurality of frequency components of the vibration frequency in response to the signal.

6. The system according to claim 5, further comprising:
   an analog digital converter in communication with the microprocessor and configured to convert the signal from a format to another format.

7. The system according to claim 5, wherein the microprocessor is further configured to determine the frequency component having the relative maximum amplitude in response to the maximum amplitude.

8. The system according to claim 7, wherein the microprocessor is further configured to identify a range of frequencies associated with the frequency component having the relative maximum amplitude.

9. The system according to claim 1, wherein the table is further configured to respond with a probable faulty component of the vehicle in response to a query including the frequency component having the relative maximum amplitude.

10. An adapter for analyzing vibration in a device having a defect, the adapter comprising:
    a receiver that receives a signal generated in response to the vibration;
    a microprocessor using a linear transform to identify a plurality of frequency components in response to the signal, the microprocessor being further configured to determine a frequency component related to the defect, wherein the microprocessor is configured to determine the defect; and
    a table configured to provide a probable faulty component of the device in response to a query, the query including the frequency component related to the defect.

11. The adapter according to claim 10, further comprising:
    a frequency selector in communication with the microprocessor, the frequency selector being configured to isolate the frequency component related to the defect.

12. The adapter according to claim 10, wherein the frequency selector further comprises:
    a signal filter to condition the signal.

13. The adapter according to claim 12, further comprising:
    a programmable gate configured to modulate the signal filter in response to instructions from the microprocessor.

14. The adapter according to claim 10, further comprising:
    an analog to digital converter to convert the signals from a format to another format.

15. An apparatus for analyzing a vibration of a device, the apparatus comprising:
    means for sensing the vibration, the vibration having a plurality of frequency components;
    means for generating a signal corresponding to the sensed vibration;
    means for determining a frequency component having a relative maximum amplitude from the plurality of frequency components;
    means for determining a probable faulty component of the device in response to the frequency component having the relative maximum amplitude;
    means for querying a table with the frequency component having the relative maximum amplitude; and
    means for returning the probable faulty component in response to the query.

16. The apparatus according to claim 15, further comprising:
    means for displaying at least one of the probable faulty component and the frequency component having the relative maximum amplitude.

17. The apparatus according to claim 15, further comprising:
    means for updating the table in response to the probable faulty component being incorrect.

18. The apparatus according to claim 15, further comprising:
    means for locating a source of the vibration.

19. The apparatus according to claim 18, further comprising:
    means for sensing the vibration at a plurality of locations; and
    means for triangulating the source of the vibration.

20. A method of analyzing a vibration of a device, the method comprising:
    sensing the vibration, the vibration having a plurality of frequency components;
    generating a signal corresponding to the sensed vibration;
    determining a frequency component having a relative maximum amplitude from the plurality of frequency components;
    determining a probable faulty component of the device in response to the frequency component having the relative maximum amplitude; and querying a table with the frequency component having the relative maximum amplitude; and returning the probable faulty component in response to the query.

21. The method according to claim 20, further comprising:

displaying at least one of the probable faulty component and the frequency component having the relative maximum amplitude.

22. The method according to claim 20, further comprising:

updating the table in response to the probable faulty component being incorrect.

23. The method according to claim 20, further comprising:

locating a source of the vibration.

24. The method according to claim 23, further comprising:

sensing the vibration at a plurality of locations; and
triangulating the source of the vibration.

* * * * *